US00PP15569P2

(12) United States Plant Patent
Olesen et al.

(10) Patent No.: US PP15,569 P2
(45) Date of Patent: Feb. 15, 2005

(54) ROSE PLANT NAMED 'POULAC013'

(50) Latin Name: *Rosa hybrida*
Varietal Denomination: POULac013

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,714

(22) Filed: Mar. 29, 2004

(51) Int. Cl.[7] ..... A01H 5/00
(52) U.S. Cl. ..... Plt./141
(58) Field of Search ..... Plt./141, 143, 148

*Primary Examiner*—Anne Marie Grunberg
*Assistant Examiner*—June Hwu

(57) ABSTRACT

A new garden rose plant of the compact floribunda class which has abundant, light pink and apricot flowers and attractive foliage. This new and distinct variety has shown to be uniform and stable in the resulting generations from asexual propagation.

2 Drawing Sheets

Botanical classification: *Rosa hybrida.*
Variety denomination: 'POULac013'.

SUMMARY OF THE INVENTION

The present invention constitutes a new and distinct variety of garden rose plant which originated from a controlled crossing between the female seed parent, an un-named seedling, and the male parent, an un-named seedling. The two parents were crossed during the summer of 1994 and the resulting seeds were planted in a controlled environment in Fredensborg, Denmark. The new variety is named 'POULac013'.

The new variety may be distinguished from its female seed parent by the following characteristics:

The seed parent has a tall growth habit, and has salmon pink flowers. 'POULac013' is compact and has light pink and apricot blend flower color.

The new variety may be distinguished from its male pollen parent by the following combination of characteristics:

The pollen parent has pink flowers while 'POULac013' has light pink and apricot blend flower color. Additionally, the pollen parent has more flower petals than 'POULac013'.

The objective of the hybridization of this rose variety was to create a new and distinct variety for garden use with unique qualities, such as:

1. Uniform and abundant light pink and apricot colored flowers;
2. Vigorous, but compact and even growth when propagated both as a budded rose and on its own roots;
3. Disease resistance.

This combination of qualities is not present in previously available commercial cultivars of this type, known to the inventors, and distinguish 'POULac013' from all other varieties of which we are aware.

As part of their rose development program, L. Pernille Olesen and Mogens N. Olesen germinated the seeds from the aforementioned hybridization during winter of 1994–1995 and conducted evaluations on the resulting seedlings in a controlled environment in Fredensborg, Denmark.

'POULac013' was selected in the spring 1995 by the inventors as a single plant from the progeny of the aforementioned hybridization.

Asexual reproduction of 'POULac013' by traditional budding and rooted cuttings was first done by L. Pernille and Mogens N. Olesen in their nursery in Fredensborg, Denmark in July, 1995. This initial and other subsequent asexual propagations conducted in controlled environments have demonstrated that the characteristics of 'POULac013' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac013'. Specifically illustrated in the first drawing;

FIG. 1.1; Open flower, stem showing cluster of open flowers, branching, and the attachment of leaves, buds, and peduncles;

FIG. 1.2; Sepals, receptacle, and peduncle;

FIG. 1.3; Flower buds at various stages of development;

FIG. 1.4; Flower petals, detached;

Specifically illustrated in the second drawing;

FIG. 2.1; Mature leaves;

FIG. 2.2; Bare stems, exhibiting thorns.

DETAILED DESCRIPTION OF THE VARIETY

The following is a description of 'POULac013', as observed in its growth in a field nursery in Jackson County, Oreg. Observed plants were budded on to *Rosa multiflora* rootstock, and are 3 years of age. Color references are made using The Royal Horticultural Society (London, England) Colour Chart, 1995, except where common terms of color are used.

For a comparison, several physical characteristics of the rose variety 'POULrek', a rose variety from the same inventors described and illustrated in U.S. Plant Pat. No. 9,688 issued Nov. 12, 1996, are compared to 'POULac013' in Chart 1.

CHART 1

| | 'POULac013' | 'POULrek' |
|---|---|---|
| Petalage | 20 petals | 25 to 30 petals |
| Flower diameter | 45 to 60 | 88 to 95 mm |
| Color of the upper surface of outer petals after flowers open. | White 155D. Yellow Group 6D to 6C. | Red 36D. Yellow 4D petal spot. |

FLOWER AND FLOWER BUD

Blooming habit: Continuous

Flower bud:

*Size.*—Upon opening, 18 mm in length from base of receptacle to end of bud. Average bud diameter is 10 mm.

*Bud form.*—Pointed ovoid slightly broad based.

*Bud color.*—As sepals unfold, petals are Red Group 45C to 45D with intonations of Red-Purple group 65A to 63A.

*Sepals.*—Upper Surface: Color: Yellow-Green Group 144B. Surface: Moderately pubescent. Lower Surface: Color: Yellow-Green Group 144A. Marginal anthocyanic pigments the color of Greyed-Red Group 182A observed. Texture: Smooth with scant stipitate glands. Sepal Shape: Sepal apex is cirrhose. Base is flat at union with receptacle. Sepal Margin: Margins have weak foliaceous appendages on three of the five sepals. Size: 20 mm (l)×5 mm (w).

*Receptacle.*—Surface Texture: Glaucous. Shape: Funnel shaped. Size: 4 m (h)×6 mm (w). Color: Yellow-Green Group 144B. Anthocyanic pigments the color of Greyed-Red Group 181A observed.

*Peduncle.*—Surface: Slightly pubescent with stipitate glands. Length: 25 to 30 mm average length. Color: Yellow-Green Group 144D. Anthocyanic pigments the color of Greyed-Red Group 181B observed. Strength: Somewhat strong.

*Borne.*—In clusters of 7 flower buds per stem.

Flower bloom:

*Fragrance.*—Moderate rose scent.

*Duration.*—The blooms have a duration on the plant on average 10 days. At full maturity, flower petals fall cleanly away from plant.

*Size.*—Flower diameter is 45 to 60 mm when open. Flower depth is 25 to 30 mm in depth.

*Form.*—General shape is a deep cup.

*Shape of flower when viewed from the side.*—Upon opening, upper part: Flat. Upon opening, lower part: Flat. Open flower, upper part: Flat. Open flower, lower part: Concave.

Petalage: 20 petals on average with 4 petaloids.

Color:

Upon opening, petals:

*Outermost petals.*—Outer side: Yellow-Orange Group 14D with marginal intonations of Orange-Red Group 32D and Red Group 36D. Inner Side: White Group 155A with intonations of Red Group 36D.

*Innermost petals.*—Outer side: Yellow-Orange Group 18D with intonations of Orange Group 32D and Red-Purple Group 63D. Inner Side: Yellow-Orange Group 18D with intonations of Yellow Group 8C at middle and basal zones.

Upon opening, basal petal spots:

*Outermost petals.*—Outer side: NONE. Inner Side: Yellow Group 6D to 6C.

*Innermost petals.*—Outer side: Yellow Group 6D to 6C. Inner Side: Yellow Group 6D to 6C.

After opening, petals:

*Outermost petals.*—Outer side: White Group 155D with light intonations Yellow Group 4D at the base and Red Group 49D at the margins. Inner Side: White Group 155D.

*Innermost petals.*—Outer side: Yellow-Orange Group 18D with marginal intonations of Orange-Red Group 32D and Red Group 36D. Inner Side: Yellow-Orange Group 18D.

After opening, basal petal spots:

*Outermost petals.*—Outer Side: NONE. Inner Side: Yellow Group 6D to 6C.

*Innermost petals.*—Outer Side: NONE. Inner Side: Yellow Group 6D to 6C.

General tonality: Open flowers are Yellow-Orange Group 21B with intonations of Orange Group 29B. No change in the general tonality at the end of the 10th day. Afterwards, general tonality changes to White Group 155D with intonations of Yellow Group 6D and Red Group 36D.

Petals:

*Petal reflex.*—Somewhat reflexed.

*Margin.*—Entire and uniform. Weak undulations of margin observed.

*Shape.*—Apex: round. Base: acute to round.

*Size.*—34 mm (l)×30 mm (w).

*Texture.*—Smooth.

*Thickness.*—Thin.

*Arrangement.*—Not Formal.

Petaloids:

*Quantity.*—3 to 6.

*Color.*—Upper Surface: Yellow Group 12D with marginal Red Group 36B. Lower Surface: Yellow Group 12D with marginal intonations of Red Group 36B.

*Size.*—25 mm (l)×20 mm (w).

Reproductive organs:

*Pistils.*—Length: 5 mm. Quantity: 42 (actual count).

*Pollen.*—Color: Yellow-Orange Group 17A. Quantity: Average.

*Anthers.*—Size: 2 mm in length. Color: Yellow-Orange Group 17A. Quantity: 103 (actual count).

*Filaments.*—Color: Yellow Group 13A. Length: 8 mm.

*Stigmas.*—Inferior relative to the filament length and height of the anthers. Color: Yellow Group 9C.

*Styles.*—Color: Yellow-Green Group 154C. Other Intonations: Greyed-Red Group 18D.

*Hips.*—None Observed in the field nursery in Jackson County Oreg.

PLANT

Plant growth: Compact, upright to bushy. When grown as a budded field grown plant on *Rosa multiflora* understock, the average height of the plant is 81 cm and the average width is 65 cm.

Stems:

*Color.*—Young wood: Yellow-Green Group 144B. Older wood: Yellow-Green Group 144B.

*Surface texture.*—Young wood: Smooth. Older wood: Smooth.

Thorns:

*Incidence.*—5 thorns per 10 cm of stem.

*Size.*—Average length: 10 mm.

*Color.*—Greyed-Yellow Group 161A.

*Shape.*—Concave.

Plant foliage: Normal number of leaflets on normal leaves in middle of the stem: 5 to 7 leaflets.

*Compound leaf size.*—110 mm in length by 70 mm wide.

*Color.*—Mature Foliage: Upper surface is: Yellow-Green Group 144A. Lower surface is: Yellow-Green Group 148C. Juvenile foliage: Upper surface is: Yellow-Green Group 144A. Lower surface is: Yellow-Green Group 148C.

Plant leaves and leaflets:

*Stipules.*—Size: 16 mm in length. Quantity: 2 per compound leaf. Margins: Finely serrated with medium stipitate glands. Color: Yellow-Green Group 144B.

*Petiole.*—Length: 25 mm. Above: Color: Yellow-Green Group 144B. Underneath: Thorns.

*Rachis.*—Length: 50 mm. Above: Color: Yellow-Green Group 144B. Underneath: Thorns.

*Leaflet.*—Size: 35 mm in length by 30 mm wide. Edge: Serrated. General Shape: Ovate. Base Shape: Acute. Apex Shape: Round. Thickness: Thick. Glossiness: Moderate. Arrangement: Odd pinnate. Venation: Reticulate.

Disease resistance: Above average resistance to mildew, rust, black spot, and Botrytis under normal growing conditions in Jackson County, Oreg.

Cold hardiness: The variety 'POULac013' has been found to be cold tolerant to USDA Cold Hardiness Zone 6.

It is claimed:

1. A new and distinct variety of rose plant of the compact floribunda rose class, substantially as herein illustrated and described as a distinct and novel rose variety due to its abundant light pink and apricot flowers, disease resistance, and extended period of bloom.

* * * * *

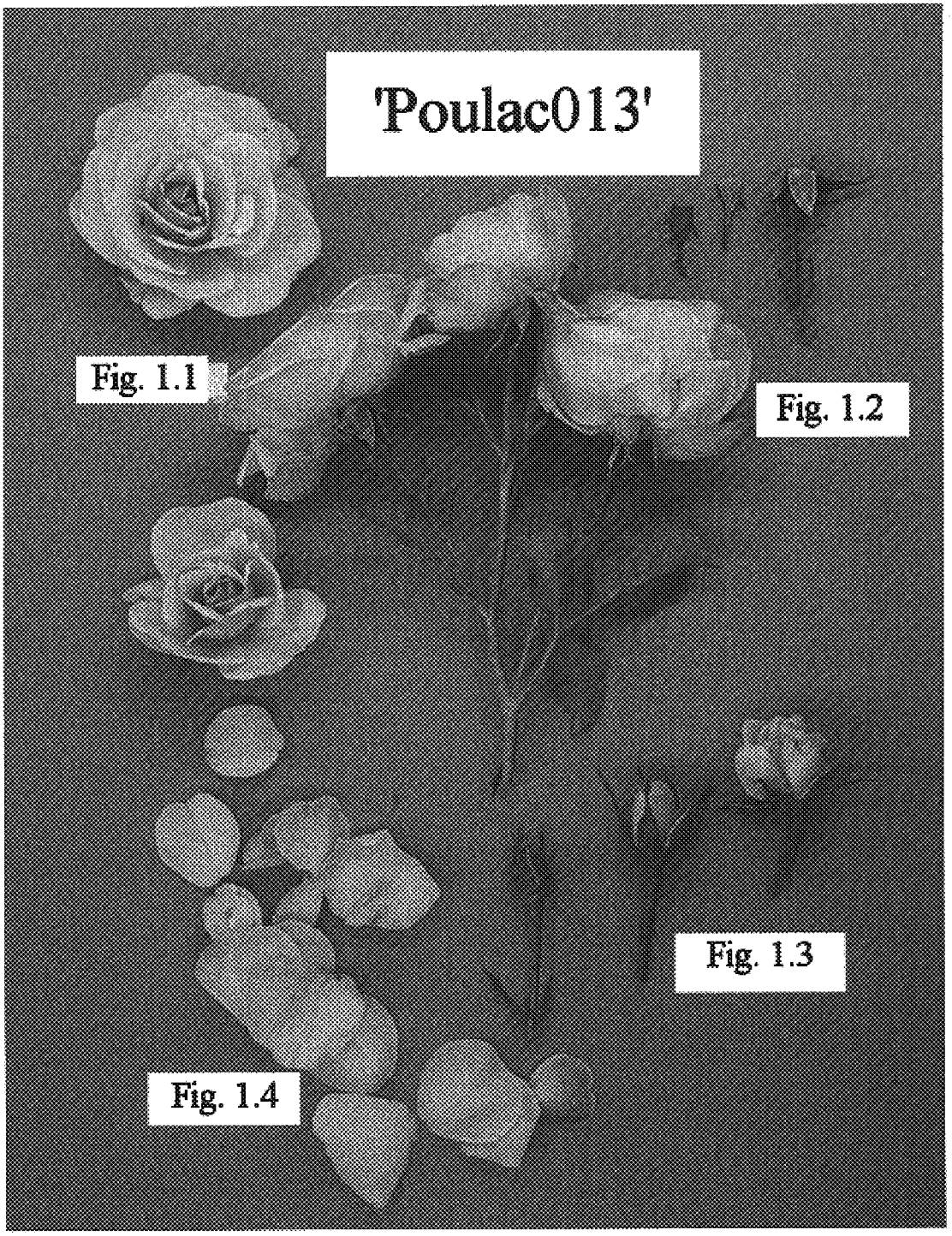
'Poulac013'
Fig. 1.1
Fig. 1.2
Fig. 1.3
Fig. 1.4

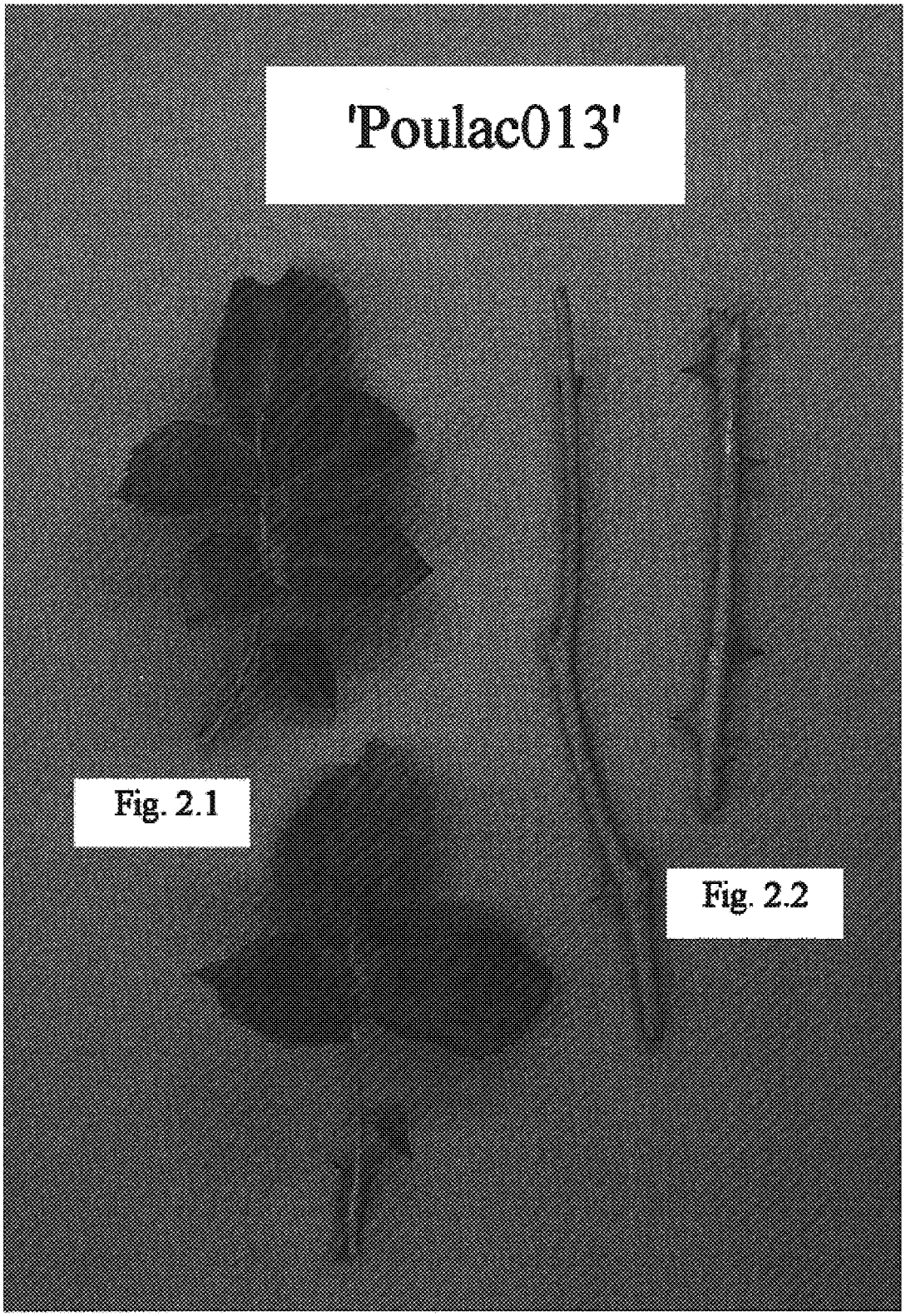
'Poulac013'
Fig. 2.1
Fig. 2.2